US011254866B2

(12) United States Patent
Jang et al.

(10) Patent No.: US 11,254,866 B2
(45) Date of Patent: Feb. 22, 2022

(54) CORE/MULTI-SHELL UPCONVERSION FLUORIDE NANOPHOSPHOR EXHIBITING LUMINESCENCE UNDER VARIOUS EXCITATION WAVELENGTHS, AND METHOD OF SYNTHESIZING THE SAME

(71) Applicant: KOREA INSTITUTE OF SCIENCE AND TECHNOLOGY, Seoul (KR)

(72) Inventors: Ho Seong Jang, Seoul (KR); A Ra Hong, Seoul (KR); So Hye Cho, Seoul (KR); Seung Yong Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 190 days.

(21) Appl. No.: 16/683,265

(22) Filed: Nov. 14, 2019

(65) Prior Publication Data
US 2020/0308484 A1  Oct. 1, 2020

(30) Foreign Application Priority Data

Mar. 27, 2019  (KR) .................. 10-2019-0035403

(51) Int. Cl.
| C09K 11/77 | (2006.01) |
| A61K 49/18 | (2006.01) |
| B42D 25/36 | (2014.01) |
| B82Y 40/00 | (2011.01) |
| B82Y 30/00 | (2011.01) |
| B82Y 5/00 | (2011.01) |

(52) U.S. Cl.
CPC ...... *C09K 11/7772* (2013.01); *A61K 49/1818* (2013.01); *A61K 49/1827* (2013.01); *B42D 25/36* (2014.10); *C09K 11/7773* (2013.01); *B82Y 5/00* (2013.01); *B82Y 30/00* (2013.01); *B82Y 40/00* (2013.01)

(58) Field of Classification Search
CPC .. C09K 11/7773; C09K 11/025; B42D 25/26; A61K 49/1818; B82Y 5/00; B82Y 40/00; B82Y 30/00
See application file for complete search history.

(56) References Cited

FOREIGN PATENT DOCUMENTS

| CN | 107033905 | * | 8/2017 |
| KR | 101792800 B1 | | 11/2017 |

OTHER PUBLICATIONS

Chen et al, Intense Visible and Near-InfraRed UpConversion Photoluminescence in Colloidal LiYF4:Er3+ Nanocrystals Under Excitation at 1490 nm, ACS Nano, vol. 5, #6, pp. 4981-4985, May 10, 2011.*
Translation for CN 107033905—Aug. 11, 2017.*
A-Ra Hong et al., "Intense Red-Emitting Upconversion Nanophosphors (800 nm-Driven) with a Core/Double-Shell Structure for Dual-Modal Upconversion Luminescence and Magnetic Resonance in Vivo Imaging Applications," ACS Applied Materials & Interfaces, Mar. 2018, pp. 12331-12340, American Chemical Society.
Francois Auzel, "Upconversion and Anti-Stokes Processes with f and d Ions in Solids," Chemical Reviews, 2004, pp. 139-174, vol. 104, No. 1, American Chemical Society.
G. Blasse et al., Luminescent Materials, 1994, pp. 40-45, Springer-Verlag Berlin Heidelberg.
Guanying Chen et al., "Upconversion emission tuning from green to red in Yb3+/Ho3+-codoped NaYF4 nanocrystals by tridoping with Ce3+ ions," Nanotechnology, 2009, 6 pages, DOI:10.1088/0957-4484/20/38/385704.
Juan Wang et al., "Single-Band Upconversion Emission in Lanthanide-Doped KMnF3 Nanocrystals," Angew. Chem. Int. Ed., 2011, pp. 10369-10372, DOI: 10.1002/anie.201104192.

* cited by examiner

*Primary Examiner* — C Melissa Koslow
(74) *Attorney, Agent, or Firm* — Cantor Colburn LLP

(57) ABSTRACT

Provided is a fluoride nanophosphor using, as cores, luminescent nanoparticles expressed by Chemical Formula 1.

$$\text{LiEr}_{1-x-y}\text{L}_y\text{F}_4\text{:Tm}^{3+}_x \quad \text{[Chemical Formula 1]}$$

(In Chemical Formula 1, x is a real number satisfying $0 \leq x \leq 0.3$, y is a real number satisfying $0 \leq y \leq 0.8$ and is selected within a range satisfying $0 \leq x+y \leq 0.9$, and L is any one selected from the group consisting of yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), ytterbium (Yb), lutetium (Lu), and a combination thereof.)

20 Claims, 19 Drawing Sheets

Embodiment 2

Embodiment 3

Embodiment 10

Embodiment 11

CORE/MULTI-SHELL UPCONVERSION FLUORIDE NANOPHOSPHOR EXHIBITING LUMINESCENCE UNDER VARIOUS EXCITATION WAVELENGTHS, AND METHOD OF SYNTHESIZING THE SAME

CROSS-REFERENCE TO RELATED PATENT APPLICATION

This application claims the benefit of Korean Patent Application No. 10-2019-0035403, filed on Mar. 27, 2019, in the Korean Intellectual Property Office, the disclosure of which is incorporated herein in its entirety by reference.

BACKGROUND

1. Field

The present invention relates to an upconversion nanophosphor and a method of synthesizing the same and, more particularly, to an upconversion fluoride nanophosphor and a method of synthesizing the same.

2. Description of the Related Art

An upconversion nanophosphor refers to a phosphor including luminescent nanoparticles having a small diameter equal to or less than 100 nm and capable of absorbing low-energy light and emitting high-energy light. A phosphor generally has a structure in which an inorganic base material is doped with a lanthanide element, and an upconversion nanophosphor generally absorbs infrared light and emits visible light [Chem. Rev. vol. 104, 139-174 (2004)]. An upconversion nanophosphor generally includes a ceramic base material doped with trivalent lanthanide ions, emits light due to 4f-4f electronic transition of the trivalent lanthanide ions, and thus exhibits luminescence of a unique color based on the type of the lanthanide element regardless of the type of the host material or the diameter of nanoparticles [Luminescent Materials (1994)].

Most upconversion nanophosphors emit green or blue light by absorbing 980-nm infrared light. However, the infrared light used as excitation light in this case penetrate deeply into a body part, whereas the green or blue light emitted from the nanophosphors does not. As such, research has been currently conducted on an upconversion nanophosphor for emitting red light by absorbing 980-nm infrared light. However, in this case, energy from erbium (Er) used as an activator is transferred to manganese (Mn) [Angew. Chem. Int. Ed. 50, 10369, (2011)], or energy from holmium (Ho) used as an activator is transferred to cerium (Ce) used as a co-sensitizer, and thus a luminescence intensity is reduced [Nanotechnology 20, 385704 (2009)]. Meanwhile, 980-nm infrared light used as excitation light is easily absorbed by water molecules and thus a part onto which the 980-nm infrared light is irradiated may be increased in temperature to kill cells or damage tissues. As such, a nanophosphor capable of exhibiting luminescence by using 800-nm infrared light has been currently reported. The currently reported upconversion nanophosphor emits red light by absorbing 980 nm infrared light and 800-nm infrared light based on energy transfer from an activator to a co-sensitizer, and thus emission of intense red light may not be easily achieved [ACS Appl. Mater. Interfaces 10, 12331 (2018)]. Therefore, when developed, an upconversion nanophosphor capable of emitting intense red light by absorbing infrared light of a wavelength other than 980 nm will be appropriately usable as a fluorescent contrast agent and will also be usable as an anti-counterfeiting security material by using properties of emitting red light under irradiation of light of various wavelengths.

SUMMARY OF THE INVENTION

The present invention provides an upconversion nanophosphor capable of emitting intense red light by absorbing infrared light of a wavelength other than 980 nm, and a method of synthesizing the same. However, the scope of the present invention is not limited thereto.

According to an aspect of the present invention, there is provided a fluoride nanophosphor using, as cores, nanoparticles expressed by Chemical Formula 1.

$$LiEr_{1-x-y}L_yF_4:Tm^{3+}{}_x \qquad \text{[Chemical Formula 1]}$$

(In Chemical Formula 1, x is a real number satisfying $0 \leq x \leq 0.3$, y is a real number satisfying $0 \leq y \leq 0.8$ and is selected within a range satisfying $0 \leq x+y \leq 0.9$, and L is any one selected from the group consisting of yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), ytterbium (Yb), lutetium (Lu), and a combination thereof.)

The fluoride nanophosphor may further include first shells surrounding at least parts of the cores, and the first shells may be made of a material expressed by Chemical Formula 2.

$$LiGd_{1-p-q}M_qF_4:Yb^{3+}{}_p \qquad \text{[Chemical Formula 2]}$$

(In Chemical Formula 2, p is a real number satisfying $0 \leq p \leq 1$, q is a real number satisfying $0 \leq q \leq 1$, p and q are selected within a range satisfying $0 \leq p+q \leq 1$, and M is any one selected from the group consisting of rare-earth elements such as Y, La, Ce, Pr, Nd, Pm, Sm, Eu, Tb, Dy, Ho, erbium (Er), thulium (Tm), and Lu, and a combination thereof.)

The fluoride nanophosphor may further include second shells surrounding at least parts of the cores and the first shells, and the second shells may be made of a material expressed by Chemical Formula 3.

$$LiY_{1-r-s-t}N_tF_4:Nd^{3+}{}_r,Yb^{3+}{}_s \qquad \text{[Chemical Formula 3]}$$

(In Chemical Formula 3, r is a real number satisfying $0 < r \leq 1$, s is a real number satisfying $0 \leq s \leq 0.5$, t is a real number satisfying $0 \leq t \leq 1$, r, s, and t are selected within a range satisfying $0 < r+s+t \leq 1$, and N is any one selected from the group consisting of rare-earth elements such as La, Ce, Pr, Pm, Sm, Eu, Gd, Tb, Dy, Ho, Tm, and Lu, and a combination thereof.)

The fluoride nanophosphor may further include third shells surrounding at least parts of the cores, the first shells, and the second shells, and the third shells may be made of a material expressed by Chemical Formula 4.

$$LiGd_{1-u}Q_uF_4 \qquad \text{[Chemical Formula 4]}$$

(In Chemical Formula 4, u is a real number satisfying $0 \leq u \leq 1$, and Q is any one selected from the group consisting of rare-earth elements such as Y, La, Ce, Pr, Sm, Eu, Tb, Dy, Ho, Yb, Er, and Lu, and a combination thereof.)

The nanophosphor consisting of the cores may have a diameter of 1 nm to 40 nm.

The nanophosphor consisting of the cores and the first shells may have a diameter of 2 nm to 60 nm.

The nanophosphor consisting of the cores, the first shells, and the second shells may have a diameter of 3 nm to 80 nm.

The nanophosphor consisting of the cores, the first shells, the second shells, and the third shells may have a diameter of 4 nm to 100 nm.

The fluoride nanophosphor may emit red light by an excitation light source having a wavelength other than 980 nm.

According to another aspect of the present invention, there is provided a method of synthesizing a fluoride nanophosphor, the method including a complex formation step for forming a complex by using a first precursor, an erbium (Er) precursor, a thulium (Tm) precursor, and a sodium (Na) precursor, a first mixture solution formation step for forming a first mixture solution including the complex, oleic acid, and 1-octadecene, a reaction solution formation step for forming a reaction solution by mixing the first mixture solution with a second mixture solution including a lithium (Li) precursor, a fluorine (F) precursor, and alcohol, and a nanoparticle formation step for forming nanoparticles by removing alcohol from the reaction solution and performing heat treatment on the alcohol-removed reaction solution, wherein the nanoparticles include fluoride nanoparticles doped with $Er^{3+}$ and expressed by Chemical Formula 1, and wherein the first precursor includes any one selected from the group consisting of a yttrium (Y) precursor, a lanthanum (La) precursor, a cerium (Ce) precursor, a praseodymium (Pr) precursor, a neodymium (Nd) precursor, a promethium (Pm) precursor, a samarium (Sm) precursor, an europium (Eu) precursor, a gadolinium (Gd) precursor, a terbium (Tb) precursor, a dysprosium (Dy) precursor, a holmium (Ho) precursor, a ytterbium (Yb) precursor, a lutetium (Lu) precursor, and a combination thereof.

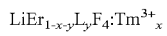  [Chemical Formula 1]

$$LiEr_{1-x-y}L_yF_4:Tm^{3+}_x$$ [Chemical Formula 1]

(In Chemical Formula 1, x is a real number satisfying $0 \leq x \leq 0.3$, y is a real number satisfying $0 \leq y \leq 0.8$ and is selected within a range satisfying $0 \leq x+y \leq 0.9$, and L is a material of the first precursor and is any one selected from the group consisting of Y, La, Ce, Pr, Nd, Pm, Sm, Eu, Gd, Tb, Dy, Ho, Yb, Lu, and a combination thereof.)

According to another aspect of the present invention, there is provided a polymer composite including the above-described fluoride nanophosphor.

According to another aspect of the present invention, there is provided a display device including the above-described fluoride nanophosphor.

According to another aspect of the present invention, there is provided a fluorescent contrast agent including the above-described fluoride nanophosphor.

According to another aspect of the present invention, there is provided an anti-counterfeiting film including the above-described fluoride nanophosphor.

According to another aspect of the present invention, there is provided a magnetic resonance imaging (MRI) contrast agent including the above-described fluoride nanophosphor.

BRIEF DESCRIPTION OF THE DRAWINGS

The above and other features and advantages of the present invention will become more apparent by describing in detail embodiments thereof with reference to the attached drawings in which.

DETAILED DESCRIPTION

Figure 1:
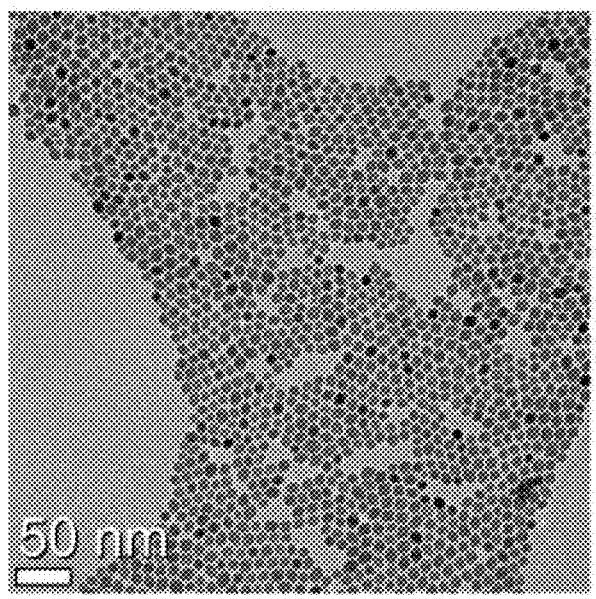
FIG. 1 illustrates a transmission electron microscopy (TEM) image of a core upconversion nanophosphor according to an embodiment of the present invention.

Hereinafter, the present invention will be described in detail by explaining embodiments of the invention with reference to the attached drawings. The invention may, however, be embodied in many different forms and should not be construed as being limited to the embodiments set forth herein; rather, these embodiments are provided so that this disclosure will be thorough and complete, and will fully convey the concept of the invention to one of ordinary skill in the art. In the drawings, the sizes of some elements may be exaggerated or reduced for convenience of explanation, and like reference numerals denote like elements.

The present invention relates to a red-emitting upconversion nanophosphor applicable to an anti-counterfeiting material, a fluorescent contrast agent, a magnetic resonance imaging (MRI) contrast agent, etc. by using invisible near infrared light as an excitation source. More particularly, the present invention relates to a highly efficient and tetragonal fluoride core/first shell/second shell/third shell (core/multi-shell) upconversion nanophosphor having a particle diameter of 1 nm to 50 nm and capable of converting near infrared light of 800-nm, 980-nm, and 1530-nm bands into visible light.

A fluoride nanophosphor according to an embodiment of the present invention includes, as cores, red-emitting nanoparticles expressed by Chemical Formula 1.

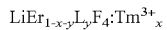  [Chemical Formula 1]

(In Chemical Formula 1, x is a real number satisfying 0≤x≤0.3, y is a real number satisfying 0≤y≤0.8 and is selected within a range satisfying 0≤x+y≤0.9, and L is any one selected from the group consisting of yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), ytterbium (Yb), lutetium (Lu), and a combination thereof.)

The fluoride nanophosphor may further include first shells surrounding at least parts of the cores, and the first shells may be made of a material expressed by Chemical Formula 2.

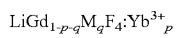  [Chemical Formula 2]

(In Chemical Formula 2, p is a real number satisfying 0≤p≤1, q is a real number satisfying 0≤q≤1, p and q are selected within a range satisfying 0≤p+q≤1, and M is any one selected from the group consisting of rare-earth elements such as Y, La, Ce, Pr, Nd, Pm, Sm, Eu, Tb, Dy, Ho, erbium (Er), thulium (Tm), and Lu, and a combination thereof.)

The fluoride nanophosphor may further include second shells surrounding at least parts of the cores and the first shells, and the second shells may be made of a material expressed by Chemical Formula 3.

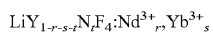  [Chemical Formula 3]

(In Chemical Formula 3, r is a real number satisfying 0<r≤1, s is a real number satisfying 0≤s≤0.5, t is a real number satisfying 0≤t≤1, r, s, and t are selected within a range satisfying 0<r+s+t≤1, and N is any one selected from the group consisting of rare-earth elements such as La, Ce, Pr, Pm, Sm, Eu, Gd, Tb, Dy, Ho, Tm, and Lu, and a combination thereof.)

The fluoride nanophosphor may further include third shells surrounding at least parts of the cores, the first shells, and the second shells, and the third shells may be made of a material expressed by Chemical Formula 4.

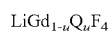  [Chemical Formula 4]

(In Chemical Formula 4, u is a real number satisfying 0≤u≤1, and Q is any one selected from the group consisting of rare-earth elements such as Y, La, Ce, Pr, Sm, Eu, Tb, Dy, Ho, Yb, Er, and Lu, and a combination thereof.)

In the fluoride nanophosphor, the nanophosphor consisting of the cores may have a diameter of 1 nm to 40 nm, the nanophosphor consisting of the cores and the first shells may have a diameter of 2 nm to 60 nm, the nanophosphor consisting of the cores, the first shells, and the second shells may have a diameter of 3 nm to 80 nm, and the nanophosphor consisting of the cores, the first shells, the second shells, and the third shells may have a diameter of 4 nm to 100 nm.

The fluoride nanophosphor may emit red light by an excitation light source having a wavelength other than 980 nm.

A method of synthesizing a fluoride nanophosphor, according to an embodiment of the present invention, includes a complex formation step for forming a complex by using a first precursor, an erbium (Er) precursor, a thulium (Tm) precursor, and a sodium (Na) precursor, a first mixture solution formation step for forming a first mixture solution including the complex, oleic acid, and 1-octadecene, a reaction solution formation step for forming a reaction solution by mixing the first mixture solution with a second mixture solution including a lithium (Li) precursor, a fluorine (F) precursor, and alcohol, and a nanoparticle formation step for forming nanoparticles by removing alcohol from the reaction solution and performing heat treatment on the alcohol-removed reaction solution, wherein the nanoparticles include fluoride nanoparticles doped with Er$^{3+}$ and expressed by Chemical Formula 1, and wherein the first precursor includes any one selected from the group consisting of a yttrium (Y) precursor, a lanthanum (La) precursor, a cerium (Ce) precursor, a praseodymium (Pr) precursor, a neodymium (Nd) precursor, a promethium (Pm) precursor, a samarium (Sm) precursor, an europium (Eu) precursor, a gadolinium (Gd) precursor, a terbium (Tb) precursor, a dysprosium (Dy) precursor, a holmium (Ho) precursor, a ytterbium (Yb) precursor, a lutetium (Lu) precursor, and a combination thereof.

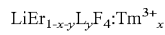  [Chemical Formula 1]

(In Chemical Formula 1, x is a real number satisfying 0≤x≤0.3, y is a real number satisfying 0≤y≤0.8 and is selected within a range satisfying 0≤x+y≤0.9, and L is a material of the first precursor and is any one selected from the group consisting of Y, La, Ce, Pr, Nd, Pm, Sm, Eu, Gd, Tb, Dy, Ho, Yb, Lu, and a combination thereof.)

The above-described fluoride nanophosphor according to an embodiment of the present invention may be used for a polymer composite, a display device, a fluorescent contrast agent, an anti-counterfeiting film, an MRI contrast agent, etc.

Red-emitting core/first shell/second shell/third shell $LiEr_{1-x-y}L_yF_4:Tm^{3+}{}_x/LiGd_{1-p-q}M_qF_4:Yb^{3+}{}_p/LiY_{1-r-s-t}N_tF_4:Nd^{3+}{}_r,Yb^{3+}{}_s/LiGd_{1-u}Q_uF_4$ upconversion nanophosphors according to embodiments of the present invention will now be described with reference to the attached drawings.

Herein, x is a real number satisfying $0 \leq x \leq 0.3$, y is a real number satisfying $0 \leq y \leq 0.8$ and is selected within a range satisfying $0 \leq x+y \leq 0.9$, L is any one selected from the group consisting of Y, La, Ce, Pr, Nd, Pm, Sm, Eu, Gd, Tb, Dy, Ho, Yb, Lu, and a combination thereof, p is a real number satisfying $0 \leq p \leq 1$, q is a real number satisfying $0 \leq q \leq 1$, p and q are selected within a range satisfying $0 \leq p+q \leq 1$, M is any one selected from the group consisting of Y, La, Ce, Pr, Nd, Pm, Sm, Eu, Tb, Dy, Ho, Er, Tm, Lu, and a combination thereof, r is a real number satisfying $0 < r \leq 1$, s is a real number satisfying $0 \leq s \leq 0.5$, t is a real number satisfying $0 \leq t \leq 1$, r, s, and t are selected within a range satisfying $0 < r+s+t \leq 1$, N is any one selected from the group consisting of La, Ce, Pr, Pm, Sm, Eu, Gd, Tb, Dy, Ho, Er, Tm, Lu, and a combination thereof, u is a real number satisfying $0 \leq u \leq 1$, and Q is any one selected from the group consisting of rare-earth elements such as Y, La, Ce, Pr, Sm, Eu, Tb, Dy, Ho, Yb, Er, and Lu, and a combination thereof.

Methods of synthesizing core/multi-shell upconversion fluoride nanophosphors, according to embodiments of the present invention, will now be described.

<Embodiment 1> Synthesis of Red-Emitting Upconversion Nanophosphor Doped with $Er^{3+}$ and $Tm^{3+}$ 0.997 mmol of erbium chloride hexahydrate ($ErCl_3 \cdot 6H_2O$), 0.003 mmol of thulium chloride hexahydrate ($TmCl_3 \cdot 6H_2O$), and 3.1 mmol of sodium oleate ($C_{18}H_{33}O_2Na$) were weighed, a mixed solvent of water, ethanol, and hexane was added by a certain amount, and then heat treatment was performed at 70° C. to form a lanthanide complex (complex formation step). The complex was mixed with a solution including oleic acid and 1-octadecene, and heat treatment was performed at 150° C. for 40 minutes to form a mixture solution including the lanthanide complex (first mixture solution formation step).

10 ml of a methanol solution including 2.5 mmol of lithium hydroxide and 4 mmol of ammonium fluoride was formed (second mixture solution formation step), and then was mixed with the mixture solution including the lanthanide complex (reaction solution formation step).

After sufficiently mixed, methanol was removed and then heat treatment was performed in an inert gas atmosphere. In this case, the heat treatment might be performed at 230° C. to 320° C. for 10 minutes to 4 hours (nanoparticle formation step). After the heat treatment was finished and a cooling process was performed to a room temperature, a colloidal nanophosphor having a diameter of 1 nm to 40 nm was obtained. The nanophosphor obtained as described above was washed with acetone or ethanol and then was dispersed and stored in a non-polar solvent such as hexane, cyclohexane, or chloroform. The nanoparticles synthesized in Embodiment 1 may be expressed by a chemical formula of $LiEr_{0.997}F_4:Tm^{3+}0.003$.

FIG. 1 illustrates a transmission electron microscopy (TEM) image of the red-emitting core upconversion nanophosphor according to Embodiment 1 of the present invention. Referring to the TEM image of FIG. 1, it is shown that the core upconversion nanophosphor has a uniform diameter and shape within 10 nm.

Figure 2:
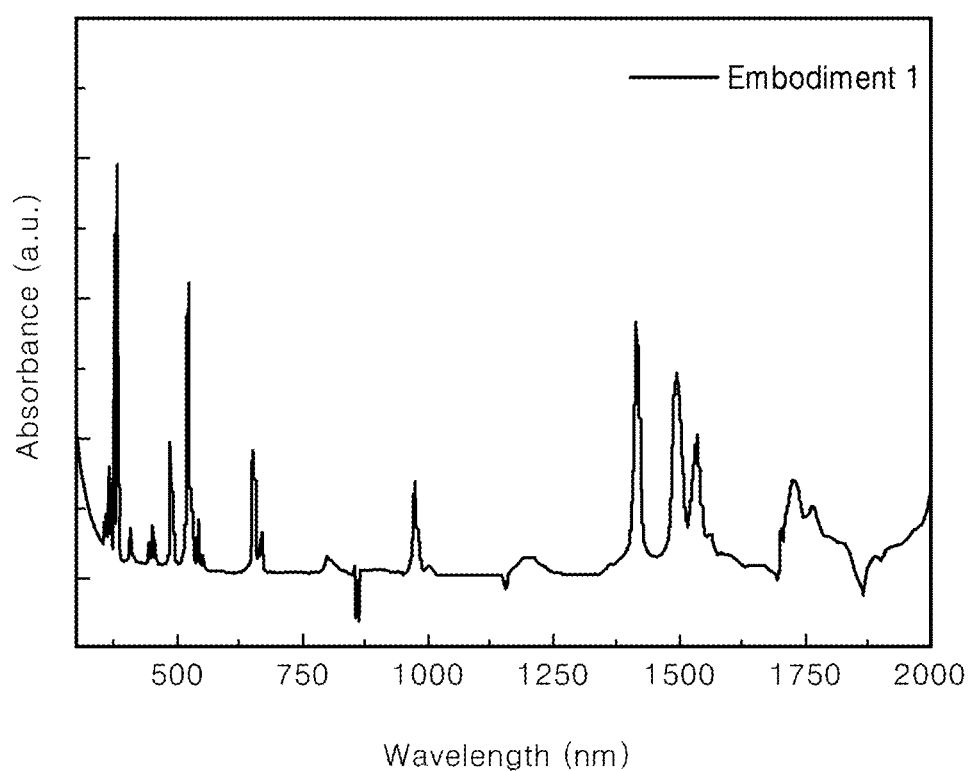
FIG. 2 illustrates an absorption spectrum of the core upconversion nanophosphor according to an embodiment of the present invention.

FIG. 2 illustrates an absorption spectrum of the red-emitting core upconversion nanophosphor according to Embodiment 1 of the present invention. Referring to the absorption spectrum of FIG. 2, it is shown that the core upconversion nanophosphor exhibits high absorption peaks in 980-nm and about 1500-nm infrared bands, and also exhibits an absorption peak in a 800-nm infrared band.

<Embodiment 2> Synthesis of Core/First Shell Red-Emitting Upconversion Nanophosphor In the current embodiment, a core/first shell nanophosphor using, as cores, the $LiEr_{0.997}F_4:Tm^{3+}{}_{0.003}$ nanoparticles synthesized in Embodiment 1, and including shells made of a $LiGdF_4$ fluoride compound was synthesized.

1 mmol of gadolinium chloride hexahydrate ($GdCl_3 \cdot 6H_2O$) was mixed with a solution including oleic acid and 1-octadecene, and heat treatment was performed at 150° C. for 30 minutes to form a mixture solution including a lanthanide complex (first mixture solution formation step).

The first mixture solution was mixed with a solution including the $LiEr_{0.997}F_4:Tm^{3+}{}_{0.003}$ nanoparticles synthesized in Embodiment 1, to form a second mixture solution (second mixture solution formation step).

10 ml of a methanol solution including 2.5 mmol of lithium hydroxide and 4 mmol of ammonium fluoride was formed (third mixture solution formation step), and then was mixed with the second mixture solution (reaction solution formation step).

After sufficiently mixed, methanol was removed and then heat treatment was performed in an inert gas atmosphere. In this case, the heat treatment might be performed at 230° C. to 320° C. for 10 minutes to 4 hours (nanoparticle formation step). After the heat treatment was finished and a cooling process was performed to a room temperature, a colloidal nanophosphor having a diameter of 2 nm to 60 nm was obtained. The nanophosphor obtained as described above was washed with acetone or ethanol and then was dispersed and stored in a non-polar solvent such as hexane, cyclohexane, or chloroform.

<Embodiment 3> Synthesis of Core/First Shell Red-Emitting Upconversion Nanophosphor Doped with $Yb^{3+}$ In the current embodiment, a core/first shell nanophosphor using, as cores, the $LiEr_{0.997}F_4:Tm^3{}_{0.003}$ nanoparticles synthesized in Embodiment 1, and including shells made of a $LiGdF_4$ fluoride compound doped with $Yb^3$ was synthesized.

0.6 mmol of gadolinium chloride hexahydrate ($GdCl_3 \cdot 6H_2O$) and 0.4 mmol of ytterbium chloride hexahydrate ($YbCl_3 \cdot 6H_2O$) were mixed with a solution including oleic acid and 1-octadecene, and heat treatment was performed at 150° C. for 30 minutes to form a mixture solution including a lanthanide complex (first mixture solution formation step).

The first mixture solution was mixed with a solution including the $LiEr_{0.997}F_4:Tm^3{}_{0.003}$ nanoparticles synthesized in Embodiment 1, to form a second mixture solution (second mixture solution formation step).

10 ml of a methanol solution including 2.5 mmol of lithium hydroxide and 4 mmol of ammonium fluoride was formed (third mixture solution formation step), and then was mixed with the second mixture solution (reaction solution formation step).

After sufficiently mixed, methanol was removed and then heat treatment was performed in an inert gas atmosphere. In this case, the heat treatment might be performed at 230° C. to 320° C. for 10 minutes to 4 hours (nanoparticle formation step). After the heat treatment was finished and a cooling process was performed to a room temperature, a colloidal nanophosphor having a diameter of 2 nm to 60 nm was obtained. The nanophosphor obtained as described above was washed with acetone or ethanol and then was dispersed and stored in a non-polar solvent such as hexane, cyclohexane, or chloroform.

Figure 3:
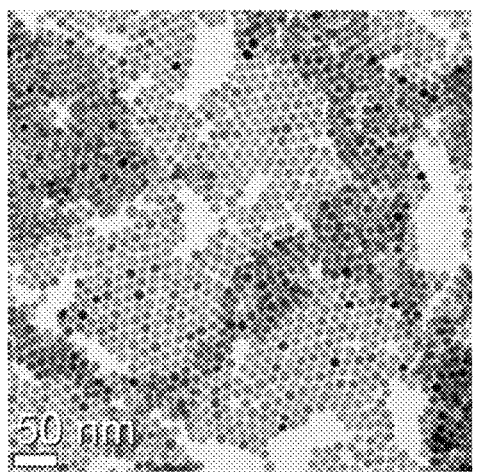
FIG. 3 illustrates TEM images of core/first shell upconversion nanophosphors according to embodiments of the present invention.
Figure 3:
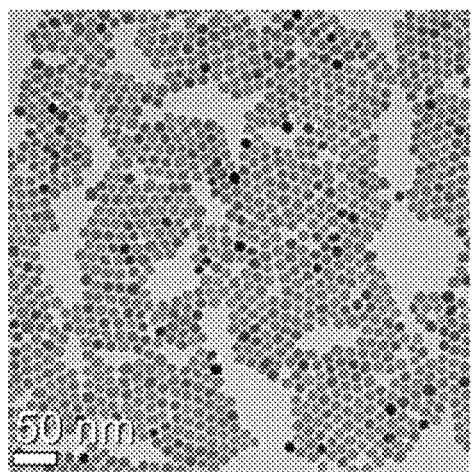
Figure 4:
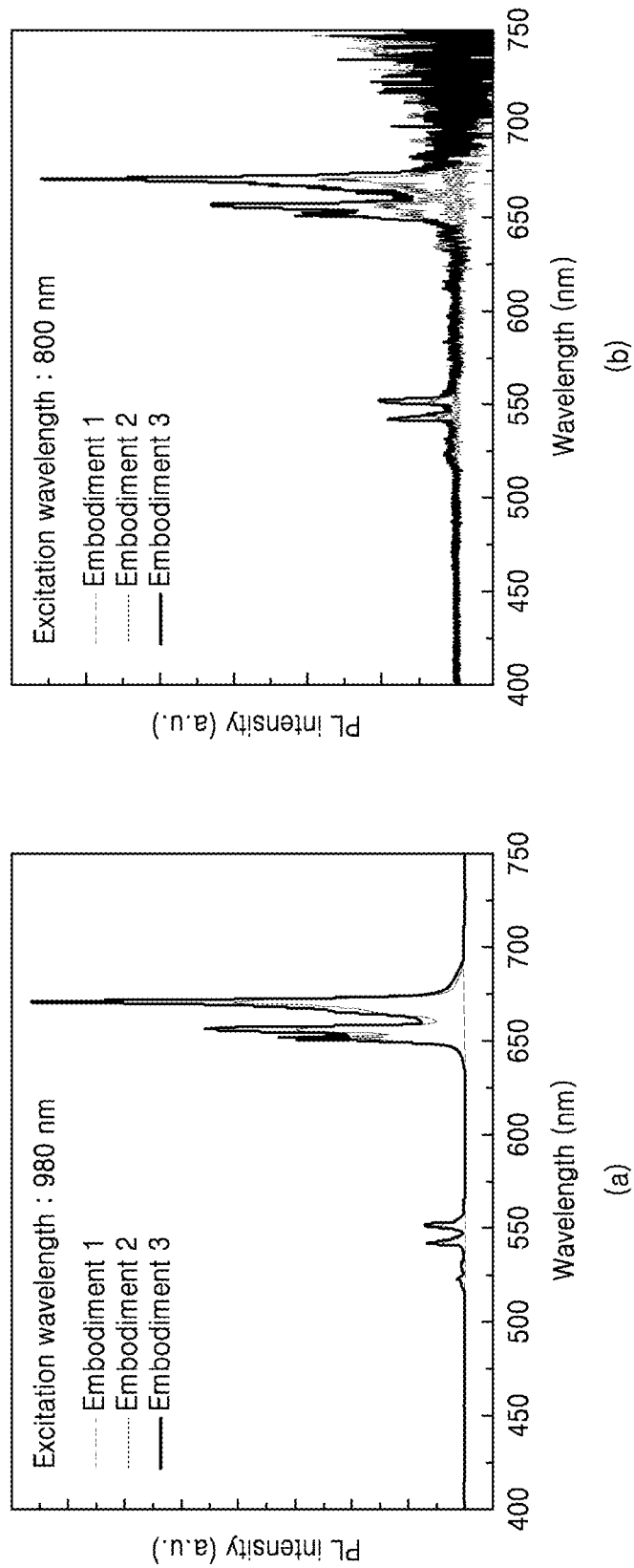
FIG. 4 illustrates photoluminescence (PL) spectra of the core and core/first shell upconversion nanophosphors according to embodiments of the present invention under 980-nm infrared excitation and 800-nm infrared excitation.

FIG. 3 illustrates TEM images of the core/first shell upconversion nanophosphors according to Embodiments 2 and 3 of the present invention. Referring to FIG. 3, it is shown that the core/first shell upconversion nanophosphors have a uniform diameter and shape of about 14 nm and that the diameter is increased due to formation of the shells around the cores. FIG. 4 illustrates photoluminescence (PL) spectra of the core and core/first shell upconversion nanophosphors according to Embodiments 1 to 3 of the present invention under 980-nm infrared excitation and 800-nm infrared excitation. FIG. 4 shows that, under 980-nm infrared excitation, the core upconversion nanophosphor (Embodiment 1) exhibits a very low PL intensity and the core/first shell upconversion nanophosphors (Embodiments 2 and 3) exhibit red PL peaks with greatly increased PL intensities. It is shown that the core/first shell upconversion nanophosphor according to Embodiment 2 exhibits a red PL intensity 572 times higher than that of the core upconversion nanophosphor according to Embodiment 1, and that the core/first shell upconversion nanophosphor according to Embodiment 3 exhibits a red PL intensity 978 times higher than that of the core upconversion nanophosphor according to Embodiment 1. It is shown that, under 800-nm infrared excitation, the core upconversion nanophosphor (Embodiment 1) does not emit red light and that the core/first shell upconversion nanophosphors (Embodiments 2 and 3) emit red light. FIG. 4 also shows that, under 980-nm infrared excitation, the core/first shell upconversion nanophosphor according to Embodiment 3 exhibits a red PL intensity about 1.5 times higher than that of the core/first shell upconversion nanophosphor according to Embodiment 2 and that, under 800-nm infrared excitation, the core/first shell upconversion nanophosphor according to Embodiment 3 exhibits a red PL intensity about 3 times higher than that of the core/first shell upconversion nanophosphor according to Embodiment 2.

<Embodiment 4> Synthesis of Core/First Shell/Second Shell Red-Emitting Upconversion Nanophosphor Doped with $Nd^{3+}$ In the current embodiment, a core/first shell/second shell nanophosphor using, as cores, the $LiEr_{0.997}F_4:Tm^{3+}_{0.003}$/$LiGdF_4$ nanoparticles synthesized in Embodiment 2, and including shells made of a $LiYF_4$ fluoride compound doped with $Nd^{3+}$ and $Yb^{3+}$ was synthesized.

0.55 mmol of yttrium chloride hexahydrate ($YCl_3 \cdot 6H_2O$), 0.4 mmol of neodymium chloride hexahydrate ($NdCl_3 \cdot 6H_2O$), and 0.05 mmol of ytterbium chloride hexahydrate ($YbCl_3 \cdot 6H_2O$) were mixed with a solution including oleic acid and 1-octadecene, and heat treatment was performed at 150° C. for 30 minutes to form a mixture solution including a lanthanide complex (first mixture solution formation step).

The first mixture solution was mixed with a solution including the $LiEr_{0.997}F_4:Tm^{3+}_{0.003}$/$LiGdF_4$ nanoparticles synthesized in Embodiment 2, to form a second mixture solution (second mixture solution formation step).

10 ml of a methanol solution including 2.5 mmol of lithium hydroxide and 4 mmol of ammonium fluoride was formed (third mixture solution formation step), and then was mixed with the second mixture solution (reaction solution formation step).

After sufficiently mixed, methanol was removed and then heat treatment was performed in an inert gas atmosphere. In this case, the heat treatment might be performed at 230° C. to 320° C. for 10 minutes to 4 hours (nanoparticle formation step). After the heat treatment was finished and a cooling process was performed to a room temperature, a colloidal nanophosphor having a diameter of 3 nm to 80 nm was obtained. The nanophosphor obtained as described above was washed with acetone or ethanol and then was dispersed and stored in a non-polar solvent such as hexane, cyclohexane, or chloroform.

Figure 5:
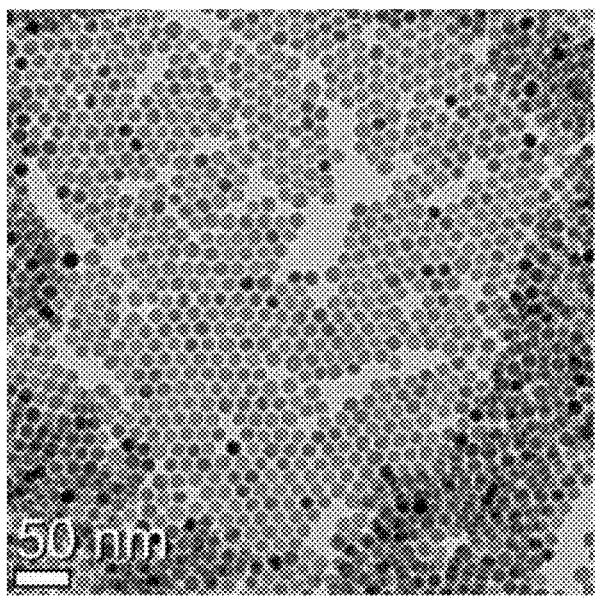
FIG. 5 illustrates a TEM image of a core/first shell/second shell upconversion nanophosphor according to an embodiment of the present invention.
Figure 6:
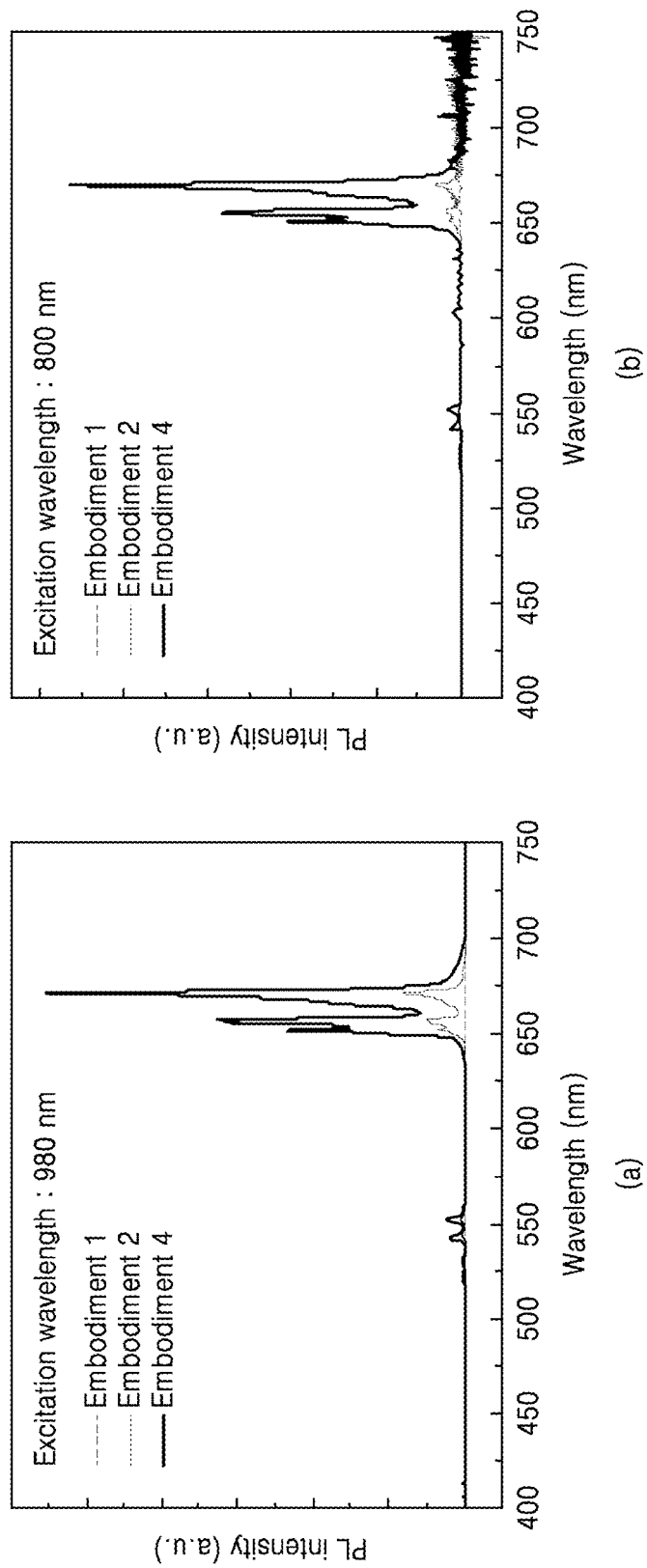
FIG. 6 illustrates PL spectra of the core, core/first shell, and core/first shell/second shell upconversion nanophosphors according to embodiments of the present invention under 980-nm infrared excitation and 800-nm infrared excitation.

FIG. 5 illustrates a TEM image of the core/first shell/second shell upconversion nanophosphor according to Embodiment 4. Referring to FIG. 5, it is shown that the synthesized core/first shell/second shell upconversion nanophosphor has a uniform diameter and shape within 16 nm and that the diameter is increased due to formation of the second shells around the cores/first shells. FIG. 6 illustrates PL spectra of the core, core/first shell, and core/first shell/second shell upconversion nanophosphors according to Embodiments 1, 2, and 4 under 980-nm infrared excitation and 800-nm infrared excitation. It is shown that, under 980-nm infrared excitation, the core/first shell/second shell upconversion nanophosphor according to Embodiment 4 exhibits a red PL intensity 6.7 times higher than that of the core/first shell upconversion nanophosphor according to Embodiment 2. It is also shown that, under 800-nm infrared excitation, the core/first shell/second shell upconversion nanophosphor according to Embodiment 4 exhibits a red PL intensity about 15 times higher than that of the core/first shell upconversion nanophosphor according to Embodiment 2.

<Embodiment 5> Synthesis of Core/First Shell/Second Shell Red-Emitting Upconversion Nanophosphor Doped with $Nd^{3+}$ In the current embodiment, a core/first shell/second shell nanophosphor using, as cores, the $LiEr_{0.997}F_4:Tm^{3+}_{0.003}$/$LiGd_{0.6}F_4:Yb^{3+}_{0.4}$ nanoparticles synthesized in Embodiment 3, and including shells made of a $LiYF_4$ fluoride compound doped with $Nd^{3+}$ and $Yb^{3+}$ was synthesized.

0.55 mmol of yttrium chloride hexahydrate ($YCl_3 \cdot 6H_2O$), 0.4 mmol of neodymium chloride hexahydrate ($NdCl_3 \cdot 6H_2O$), and 0.05 mmol of ytterbium chloride hexahydrate ($YbCl_3 \cdot 6H_2O$) were mixed with a solution including oleic acid and 1-octadecene, and heat treatment was performed at 150° C. for 30 minutes to form a mixture solution including a lanthanide complex (first mixture solution formation step).

The first mixture solution was mixed with a solution including the $LiEr_{0.997}F_4:Tm^{3+}_{0.003}$/$LiGd_{0.6}F_4:Yb^{3+}0.4$ nanoparticles synthesized in Embodiment 3, to form a second mixture solution (second mixture solution formation step).

10 ml of a methanol solution including 2.5 mmol of lithium hydroxide and 4 mmol of ammonium fluoride was formed (third mixture solution formation step), and then was mixed with the second mixture solution (reaction solution formation step).

After sufficiently mixed, methanol was removed and then heat treatment was performed in an inert gas atmosphere. In this case, the heat treatment might be performed at 230° C. to 320° C. for 10 minutes to 4 hours (nanoparticle formation step). After the heat treatment was finished and a cooling process was performed to a room temperature, a colloidal nanophosphor having a diameter of 3 nm to 80 nm was obtained. The nanophosphor obtained as described above was washed with acetone or ethanol and then was dispersed and stored in a non-polar solvent such as hexane, cyclohexane, or chloroform.

Figure 7:
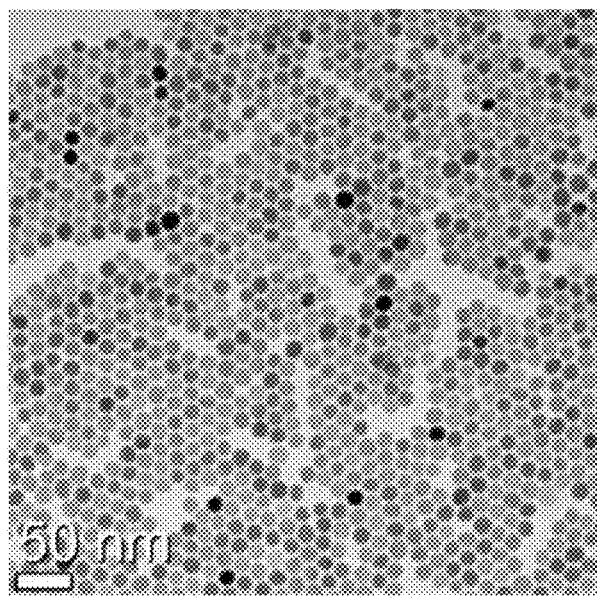
FIG. 7 illustrates a TEM image of a core/first shell/second shell upconversion nanophosphor according to another embodiment of the present invention.
Figure 8:
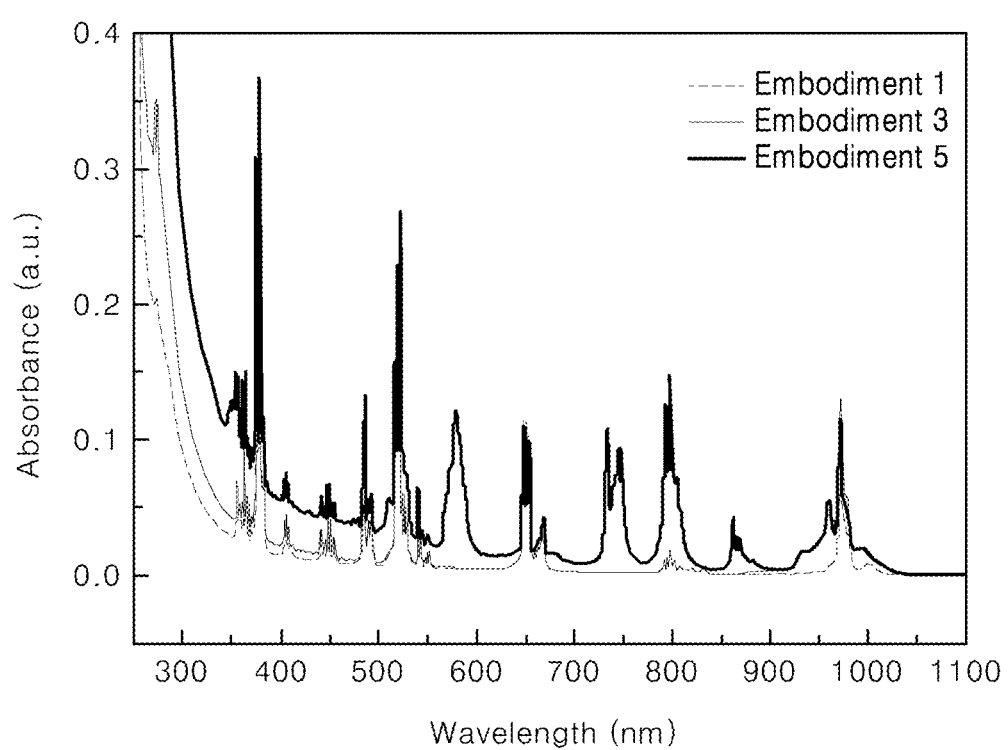
FIG. 8 illustrates absorption spectra of the core, core/first shell, and core/first shell/second shell upconversion nanophosphors according to embodiments of the present invention.

FIG. 7 illustrates a TEM image of the core/first shell/second shell upconversion nanophosphor according to Embodiment 5. Referring to FIG. 7, it is shown that the synthesized core/first shell/second shell upconversion nanophosphor has a uniform diameter and shape of about 16 nm and that the diameter is increased due to formation of the second shells around the cores/first shells. FIG. 8 illustrates absorption spectra of the core, core/first shell, and core/first shell/second shell upconversion nanophosphors according to Embodiments 1, 3, and 5. The absorption spectrum of the core upconversion nanophosphor shows an absorption peak of $Er^{3+}$, the absorption spectrum of the core/first shell upconversion nanophosphor shows an absorption peak of $Yb^{3+}$ in a 960-nm wavelength band, and the absorption spectrum of the core/first shell/second shell upconversion nanophosphor shows an absorption peak of $Nd^{3+}$ in a 800-nm wavelength band.

Figure 9:
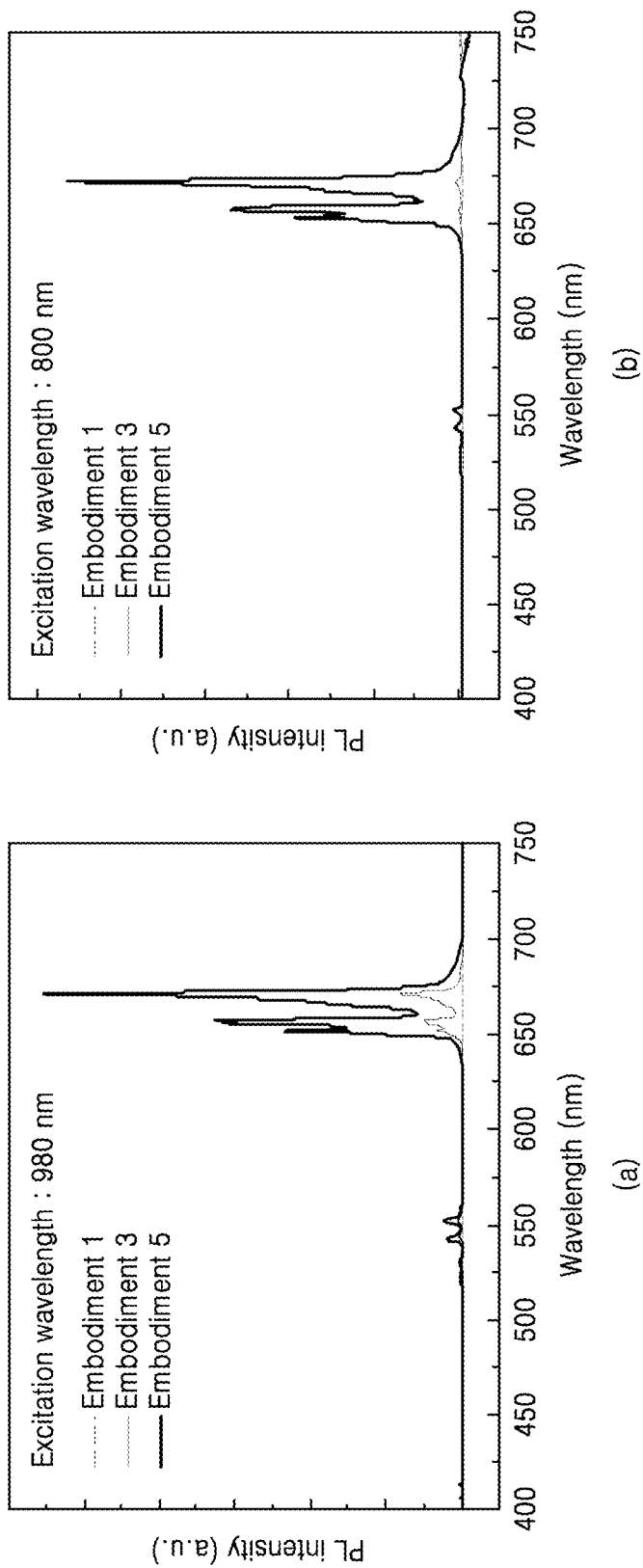
FIG. 9 illustrates PL spectra of the core, core/first shell, and core/first shell/second shell upconversion nanophosphors according to embodiments of the present invention under 980-nm infrared excitation and 800-nm infrared excitation.

FIG. 9 illustrates PL spectra of the core, core/first shell, and core/first shell/second shell upconversion nanophosphors according to Embodiments 1, 3, and 5 under 980-nm infrared excitation and 800-nm infrared excitation. It is shown that, under 980-nm infrared excitation, the core/first shell/second shell upconversion nanophosphor according to Embodiment 5 exhibits a red PL intensity about 6 times higher than that of the core/first shell upconversion nanophosphor according to Embodiment 3. It is also shown that, under 800-nm infrared excitation, the core/first shell/second shell upconversion nanophosphor according to Embodiment 5 exhibits a red PL intensity about 58 times higher than that of the core/first shell upconversion nanophosphor according to Embodiment 3.

Figure 10:
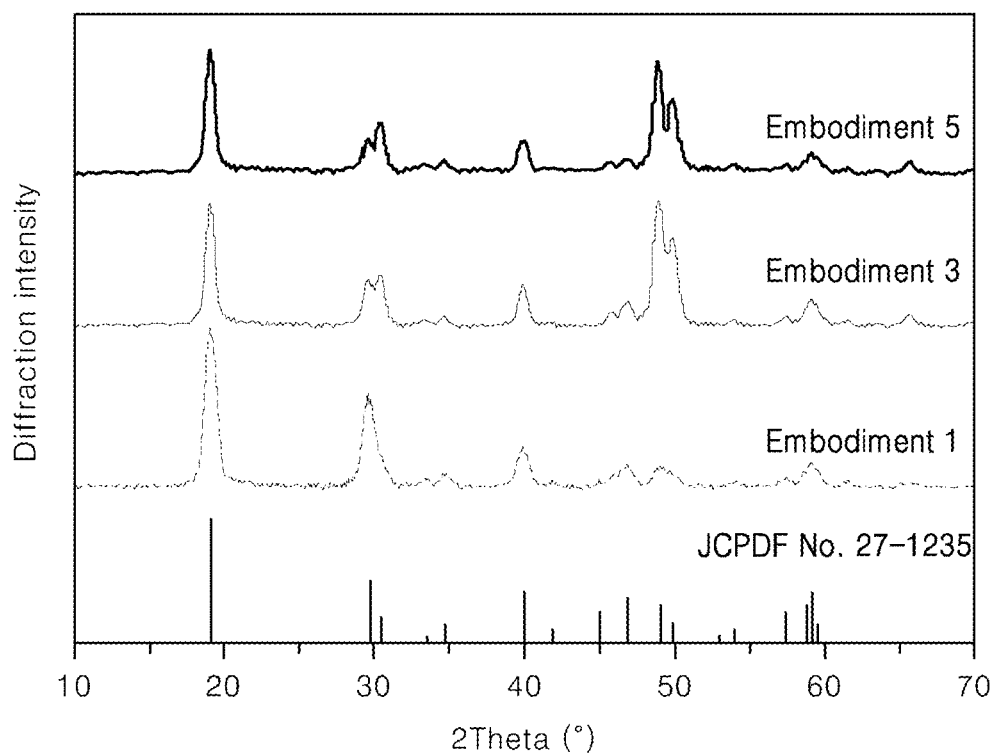
FIG. 10 illustrates X-ray diffraction patterns of the core, core/first shell, and core/first shell/second shell upconversion nanophosphors according to embodiments of the present invention.

FIG. 10 illustrates X-ray diffraction patterns of the core, core/first shell, and core/first shell/second shell upconversion nanophosphors according to Embodiments 1, 3, and 5. FIG. 10 shows that the synthesized core, core/first shell, and core/first shell/second shell upconversion nanophosphors have a single tetragonal crystal structure.

<Embodiment 6> Synthesis of Core/First Shell/Second Shell/Third Shell Red-Emitting Upconversion Nanophosphor In the current embodiment, a core/first shell/second shell/third shell nanophosphor using, as cores, the $LiEr_{0.997}F_4:Tm^{3+}_{0.003}/LiGd_{0.6}F_4:Yb^{3+}_{0.4}/LiYF_4:Nd^{3+}_{0.4},Yb^{3+}_{0.05}$ nanoparticles synthesized in Embodiment 5, and including shells made of a $LiGdF_4$ fluoride compound was synthesized.

1 mmol of gadolinium chloride hexahydrate ($GdCl_3 \cdot 6H_2O$) was mixed with a solution including oleic acid and 1-octadecene, and heat treatment was performed at 150° C. for 30 minutes to form a mixture solution including a lanthanide complex (first mixture solution formation step).

The first mixture solution was mixed with a solution including the $LiEr_{0.997}F_4:Tm^{3+}_{0.003}/LiGd_{0.6}F_4:Yb^{3+}_{0.4}/LiYF_4:Nd^{3+}_{0.4},Yb^{3+}_{0.05}$ nanoparticles synthesized in Embodiment 5, to form a second mixture solution (second mixture solution formation step).

10 ml of a methanol solution including 2.5 mmol of lithium hydroxide and 4 mmol of ammonium fluoride was formed (third mixture solution formation step), and then was mixed with the second mixture solution (reaction solution formation step).

After sufficiently mixed, methanol was removed and then heat treatment was performed in an inert gas atmosphere. In this case, the heat treatment might be performed at 230° C. to 320° C. for 10 minutes to 4 hours (nanoparticle formation step). After the heat treatment was finished and a cooling process was performed to a room temperature, a colloidal nanophosphor having a diameter of 4 nm to 100 nm was obtained. The nanophosphor obtained as described above was washed with acetone or ethanol and then was dispersed and stored in a non-polar solvent such as hexane, cyclohexane, or chloroform.

Figure 11:
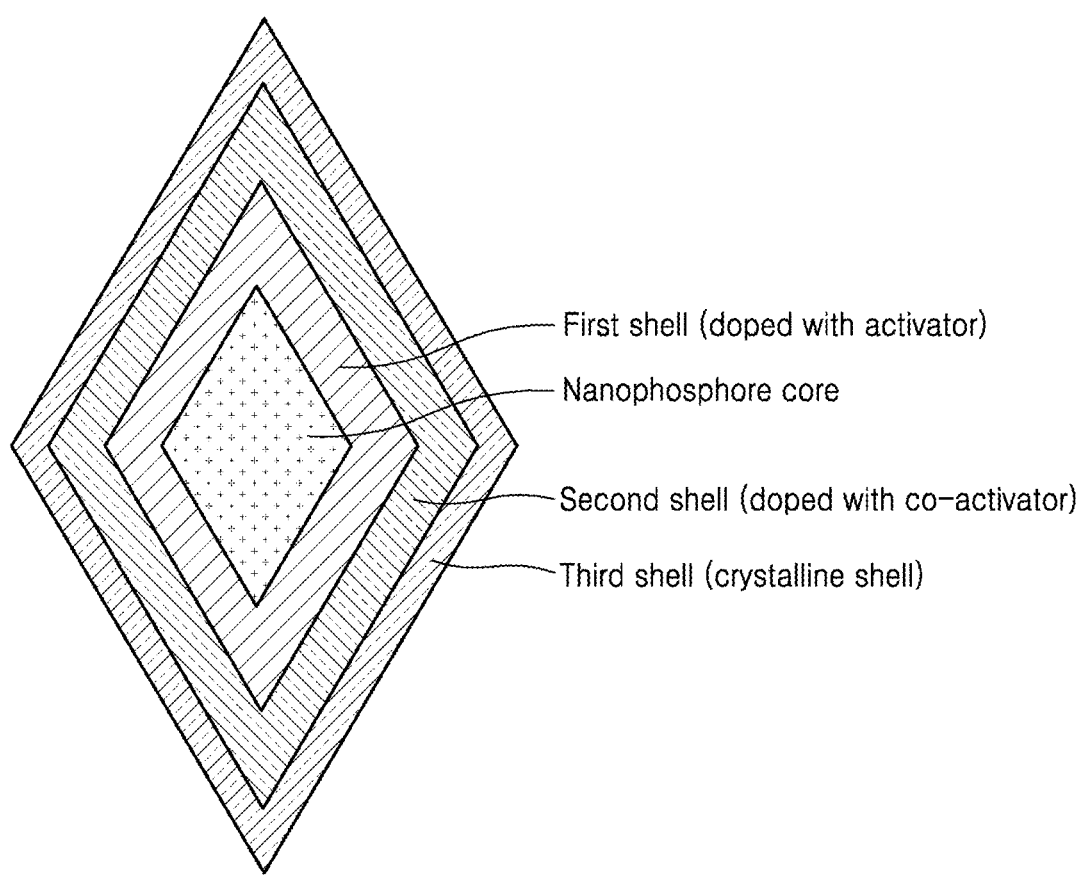
FIG. 11 illustrates a schematic cross-sectional image of a core/first shell/second shell/third shell upconversion nanophosphor according to an embodiment of the present invention.

FIG. 11 illustrates a schematic cross-sectional image of the core/first shell/second shell/third shell upconversion nanophosphor according to Embodiment 6. It is shown that a red light-emitting core is surrounded by first shell doped with a co-sensitizer capable of absorbing 980-nm infrared light, the first shell is surrounded by second shell doped with a co-sensitizer capable of absorbing 800-nm infrared light, and the second shell is surrounded by the third shell capable of reducing surface defects.

Figure 12:
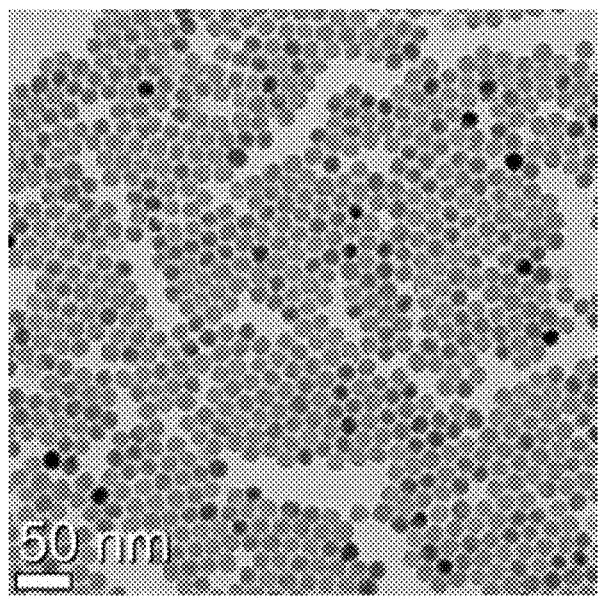
FIG. 12 illustrates a TEM image of the core/first shell/second shell/third shell upconversion nanophosphor according to an embodiment of the present invention.

FIG. 12 illustrates a TEM image of the core/first shell/second shell/third shell upconversion nanophosphor according to Embodiment 6. It is shown that the synthesized core/first shell/second shell/third shell upconversion nanophosphor has a uniform diameter and shape of about 18 nm and that the diameter of the nanoparticles is increased due to formation of the $LiGdF_4$ shells around the cores/first shells/second shells.

Figure 13:
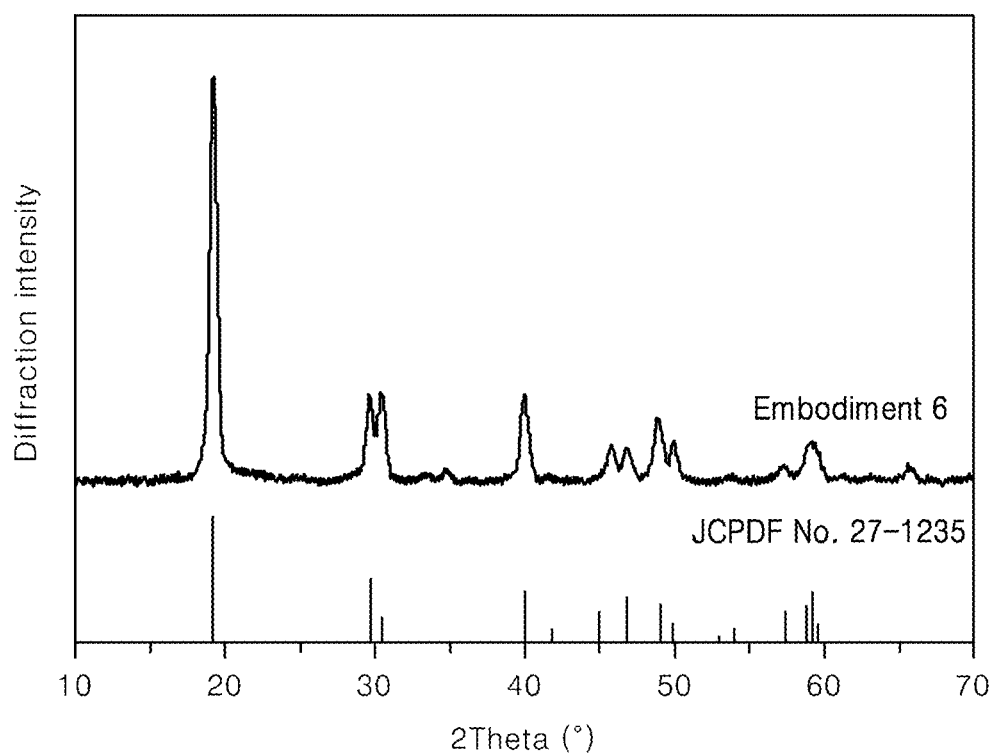
FIG. 13 illustrates an X-ray diffraction pattern of the core/first shell/second shell/third shell upconversion nanophosphor according to an embodiment of the present invention.

An X-ray diffraction pattern of the core/first shell/second shell/third shell upconversion nanophosphor, which is illustrated in FIG. 13, shows that the synthesized nanophosphor has a single tetragonal crystal structure.

Figure 14:
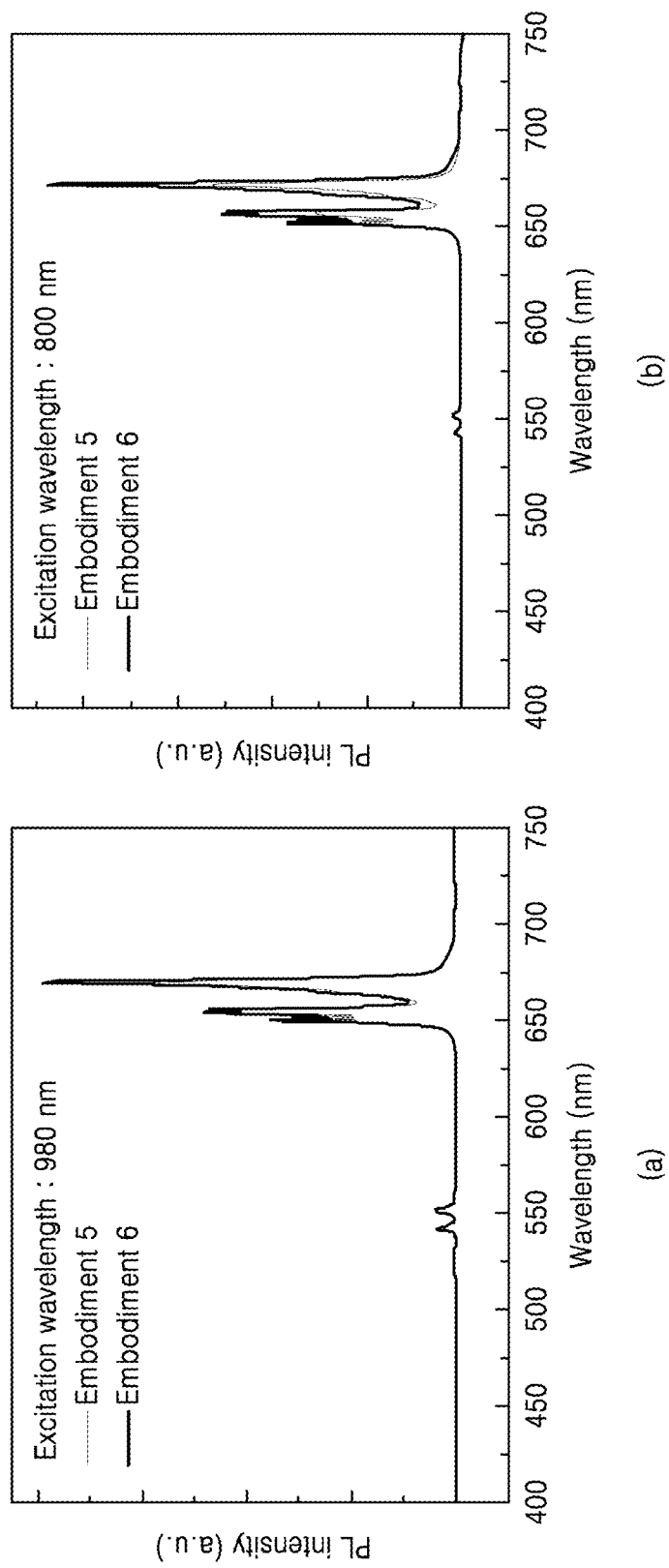
FIG. 14 illustrates PL spectra of the core/first shell/second shell and core/first shell/second shell/third shell upconversion nanophosphors according to embodiments of the present invention under 980-nm infrared excitation and 800-nm infrared excitation.

FIG. 14 illustrates PL spectra of the core/first shell/second shell and core/first shell/second shell/third shell upconversion nanophosphors according to Embodiments 5 and 6 under 980-nm infrared excitation and 800-nm infrared excitation. FIG. 14 shows that, under 980-nm infrared excitation, the core/first shell/second shell/third shell upconversion nanophosphor according to Embodiment 6 exhibits a red PL intensity 1.2 times higher than that of the core/first shell/second shell upconversion nanophosphor according to Embodiment 5 and that, under 800-nm infrared excitation, the core/first shell/second shell/third shell upconversion nanophosphor exhibits a red PL intensity 1.6 times higher than that of the core/first shell/second shell upconversion nanophosphor.

Figure 15:
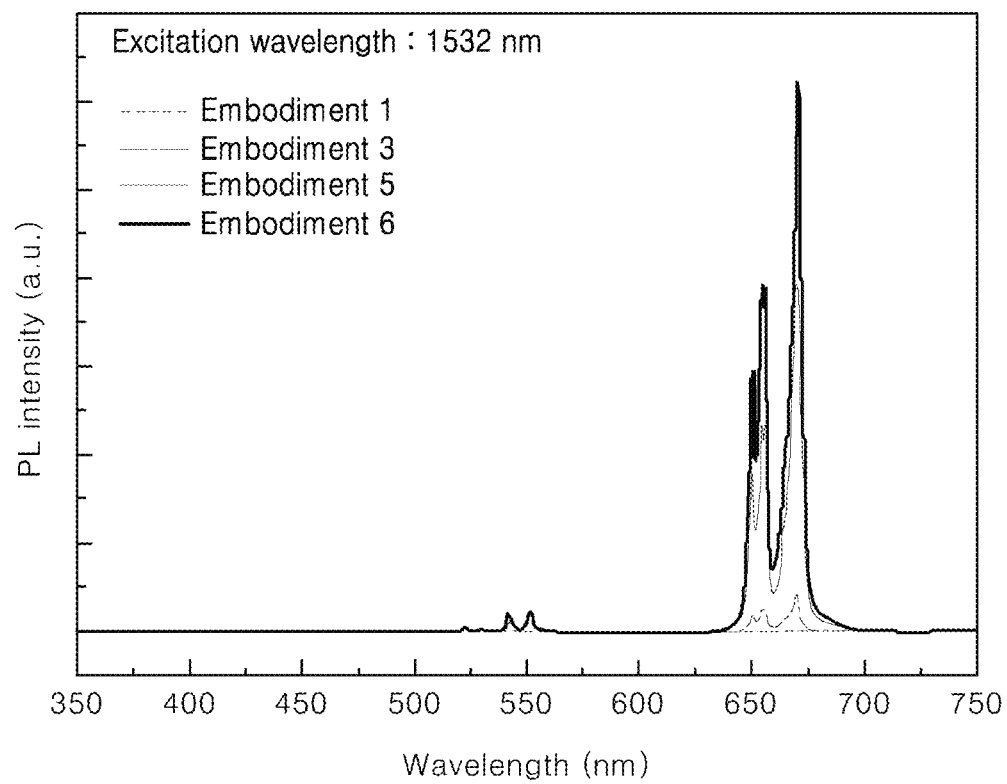
FIG. 15 illustrates PL spectra of the core, core/first shell, core/first shell/second shell, and core/first shell/second shell/third shell upconversion nanophosphors according to embodiments of the present invention under 1532-nm infrared excitation.

FIG. 15 illustrates PL spectra of the core, core/first shell, core/first shell/second shell, and core/first shell/second shell/third shell upconversion nanophosphors according to Embodiments 1, 3, 5, and 6 under 1532-nm infrared excitation, and shows that, under 1532-nm infrared excitation, the core/first shell, core/first shell/second shell, and core/first shell/second shell/third shell upconversion nanophosphors exhibit high red PL peaks, and that the core/first shell/second shell/third shell upconversion nanophosphor exhibits the highest red PL intensity.

<Embodiment 7> Manufacturing of Transparent Core/First Shell/Second Shell/Third Shell Red-Emitting Upconversion Nanophosphor Film In the current embodiment, a transparent film was manufactured by mixing polymethyl methacrylate (PMMA) polymer with the $LiEr_{0.997}F_4:Tm^{3+}{}_{0.003}/LiGd_{0.6}F_4:Yb^{3+}{}_{0.4}/LiYF_4:Nd^{3+}{}_{0.4},Yb^{3+}{}_{0.05}/LiGdF_4$ upconversion nanophosphor synthesized in Embodiment 6. 5 ml of a PMMA (950 PMMA C4) solution was mixed with 0.2 ml of a solution including the core/first shell/second shell/third shell upconversion nanophosphor synthesized in Embodiment 6, a spin coating process was performed, and then heat treatment was performed at 90° C. for 5 minutes to manufacture a nanophosphor-PMMA film.

Figure 16:
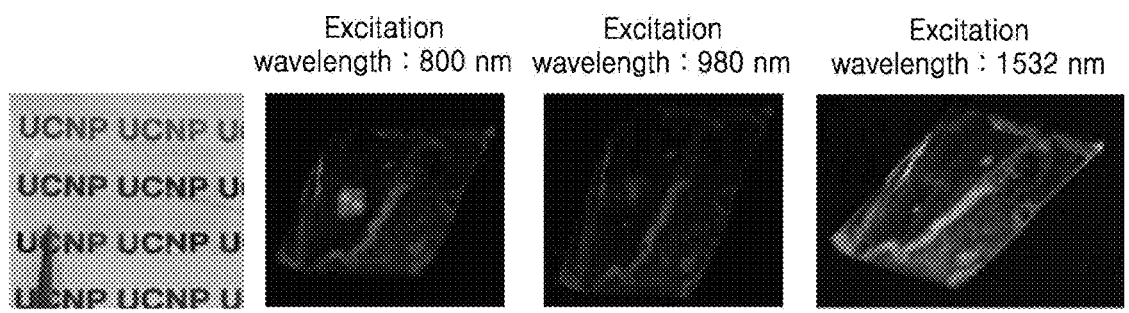
FIG. 16 illustrate photographic images of an upconversion nanophosphor-polymer film according to an embodiment of the present invention.

Photographic images of the nanophosphor-PMMA film, which are illustrated in FIG. 16, show that the PMMA polymer film including the nanophosphor is highly transparent and emits intense red light at various infrared excitation wavelengths such as 800 nm, 980 nm, and 1532 nm. Using such properties, the nanophosphor-PMMA film may be used as an anti-counterfeiting film.

<Embodiment 8> Synthesis of Upconversion Nanophosphor Doped with $Er^{3+}$ 1 mmol of erbium chloride hexahydrate ($ErCl_3.6H_2O$) and 3.1 mmol of sodium oleate ($C_{18}H_{33}O_2Na$) were weighed, a mixture solvent of water, ethanol, and hexane was added by a certain amount, and then heat treatment was performed at 70° C. to form a lanthanide complex (complex formation step). The complex was mixed with a solution including oleic acid and 1-octadecene, and heat treatment was performed at 150° C. for 40 minutes to form a mixture solution including the lanthanide complex (first mixture solution formation step).

10 ml of a methanol solution including 2.5 mmol of lithium hydroxide and 4 mmol of ammonium fluoride was formed (second mixture solution formation step), and then was mixed with the mixture solution including the lanthanide complex (reaction solution formation step).

After sufficiently mixed, methanol was removed and then heat treatment was performed in an inert gas atmosphere. In this case, the heat treatment might be performed at 230° C. to 320° C. for 10 minutes to 4 hours (nanoparticle formation step). After the heat treatment was finished and a cooling process was performed to a room temperature, a colloidal nanophosphor having a diameter of 1 nm to 40 nm was obtained. The nanophosphor obtained as described above was washed with acetone or ethanol and then was dispersed and stored in a non-polar solvent such as hexane, cyclohexane, or chloroform.

Figure 17:
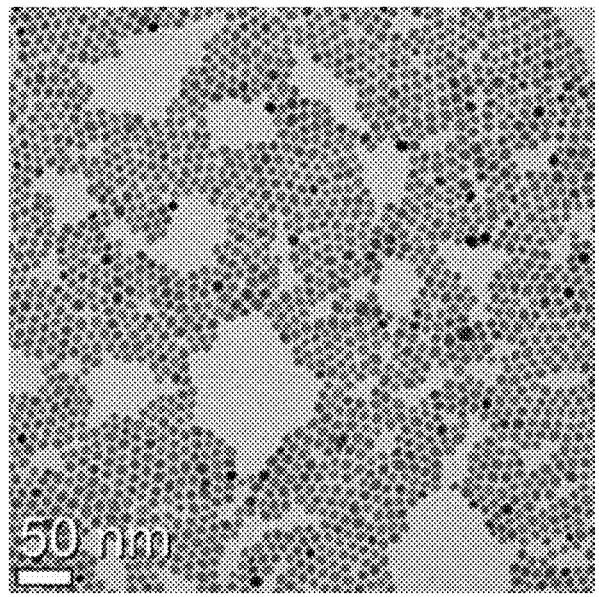
FIG. 17 illustrates a TEM image of a core upconversion nanophosphor according to another embodiment of the present invention.

FIG. 17 illustrates a TEM image of the red-emitting core upconversion nanophosphor according to Embodiment 8 of the present invention. Referring to the TEM image of FIG. 17, it is shown that the core upconversion nanophosphor has a uniform diameter and shape of about 10 nm.

<Embodiment 9> Synthesis of Core/First Shell Red-Emitting Upconversion Nanophosphor In Embodiment 9, a core/first shell nanophosphor using, as cores, the $LiErF_4$ nanoparticles synthesized in Embodiment 8, and including shells made of a $LiGdF_4$ fluoride compound was synthesized.

1 mmol of gadolinium chloride hexahydrate ($GdCl_3.6H_2O$) was mixed with a solution including oleic acid and 1-octadecene, and heat treatment was performed at 150° C. for 30 minutes to form a mixture solution including a lanthanide complex (first mixture solution formation step).

The first mixture solution was mixed with a solution including the $LiErF_4$ nanoparticles synthesized in Embodiment 8, to form a second mixture solution (second mixture solution formation step).

10 ml of a methanol solution including 2.5 mmol of lithium hydroxide and 4 mmol of ammonium fluoride was formed (third mixture solution formation step), and then was mixed with the second mixture solution (reaction solution formation step).

After sufficiently mixed, methanol was removed and then heat treatment was performed in an inert gas atmosphere. In this case, the heat treatment might be performed at 230° C. to 320° C. for 10 minutes to 4 hours (nanoparticle formation step). After the heat treatment was finished and a cooling process was performed to a room temperature, a colloidal nanophosphor having a diameter of 2 nm to 60 nm was obtained. The nanophosphor obtained as described above was washed with acetone or ethanol and then was dispersed and stored in a non-polar solvent such as hexane, cyclohexane, or chloroform.

Figure 18:
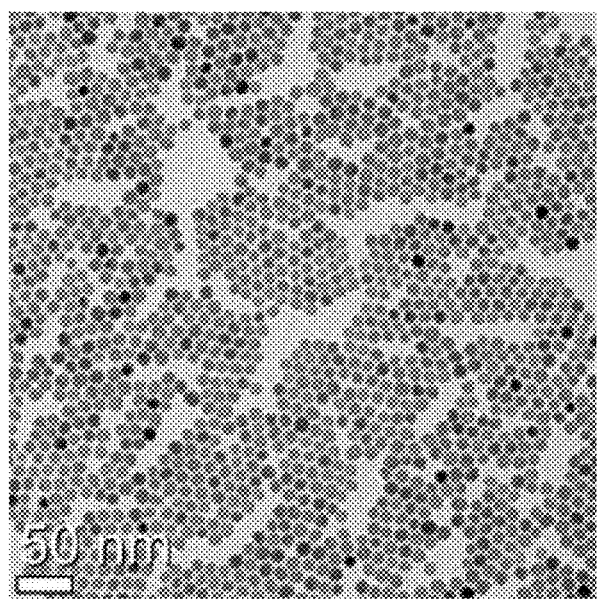
FIG. 18 illustrates a TEM image of a core/first shell upconversion nanophosphor according to another embodiment of the present invention.

FIG. 18 illustrates a TEM image of the nanophosphor according to Embodiment 9 of the present invention, and shows that the diameter of the nanophosphor is increased due to formation of the first shells.

Figure 19:
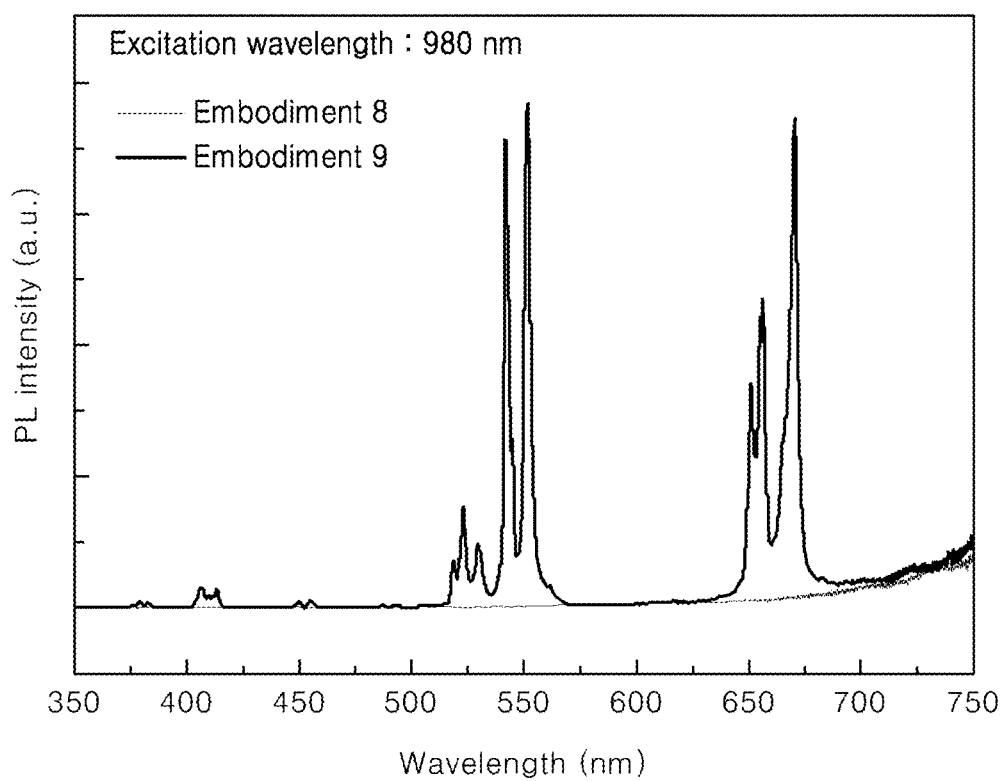
FIG. 19 illustrates PL spectra of the core and core/first shell upconversion nanophosphors according to other embodiments of the present invention under 980-nm infrared excitation and 800-nm infrared excitation.

FIG. 19 illustrates PL spectra of the nanophosphors according to Embodiments 8 and 9 of the present invention. It is shown that the PL intensity is greatly increased due to formation of the first shells around the cores.

<Embodiment 10> Synthesis of Red-Emitting Upconversion Nanophosphor Doped with $Er^{3+}$ and $Ho^{3+}$ 0.997 mmol of erbium chloride hexahydrate ($ErCl_3.6H_2O$), 0.003 mmol of holmium chloride hexahydrate ($HoCl_3.6H_2O$), and 3.1 mmol of sodium oleate ($C_{18}H_{33}O_2Na$) were weighed, a mixture solvent of water, ethanol, and hexane was added by a certain amount, and then heat treatment was performed at 70° C. to form a lanthanide complex (complex formation step). The complex was mixed with a solution including oleic acid and 1-octadecene, and heat treatment was performed at 150° C. for 40 minutes to form a mixture solution including the lanthanide complex (first mixture solution formation step).

10 ml of a methanol solution including 2.5 mmol of lithium hydroxide and 4 mmol of ammonium fluoride was formed (second mixture solution formation step), and then was mixed with the mixture solution including the lanthanide complex (reaction solution formation step).

After sufficiently mixed, methanol was removed and then heat treatment was performed in an inert gas atmosphere. In this case, the heat treatment might be performed at 230° C. to 320° C. for 10 minutes to 4 hours (nanoparticle formation step). After the heat treatment was finished and a cooling process was performed to a room temperature, a colloidal nanophosphor having a diameter of 1 nm to 40 nm was obtained. The nanophosphor obtained as described above was washed with acetone or ethanol and then was dispersed and stored in a non-polar solvent such as hexane, cyclohexane, or chloroform. The nanoparticles synthesized in Embodiment 10 may be expressed by a chemical formula of $LiEr_{0.997}Ho_{0.003}F_4$. The chemical formula of Embodiment 10 may also be expressed by $LiEr_{0.997}F_4:Ho^3+0.003$.

Figure 20:
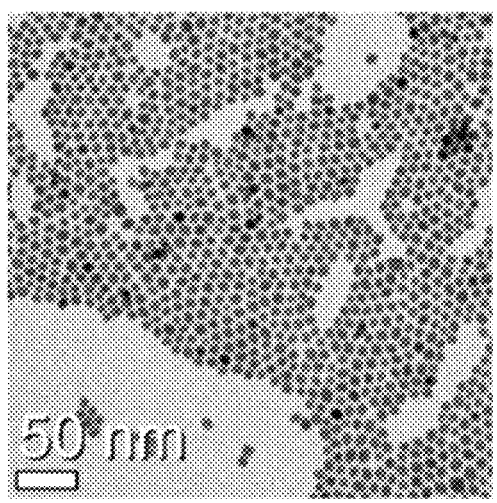
FIG. 20 illustrates TEM images of core and core/first shell upconversion nanophosphors according to other embodiments of the present invention.
Figure 20:
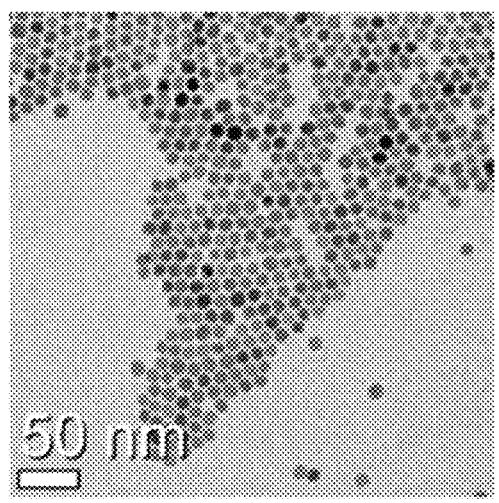

FIG. 20 illustrates a TEM image of the red-emitting upconversion nanophosphor core according to Embodiment 10 of the present invention. Referring to the TEM image of FIG. 20, it is shown that the core upconversion nanophosphor has a uniform diameter and shape within 10 nm.

<Embodiment 11> Synthesis of Core/First Shell Red-Emitting Upconversion Nanophosphor In Embodiment 11, a core/first shell nanophosphor using, as cores, the $LiEr_{0.997}Ho_{0.003}F_4$ nanoparticles synthesized in Embodiment 10, and including shells made of a LiGdF$_4$ fluoride compound was synthesized.

1 mmol of gadolinium chloride hexahydrate (GdCl$_3$·6H$_2$O) was mixed with a solution including oleic acid and 1-octadecene, and heat treatment was performed at 150° C. for 30 minutes to form a mixture solution including a lanthanide complex (first mixture solution formation step).

The first mixture solution was mixed with a solution including the LiEr$_{0.997}$Ho$_{0.003}$F$_4$ nanoparticles synthesized in Embodiment 10, to form a second mixture solution (second mixture solution formation step).

10 ml of a methanol solution including 2.5 mmol of lithium hydroxide and 4 mmol of ammonium fluoride was formed (third mixture solution formation step), and then was mixed with the second mixture solution (reaction solution formation step).

After sufficiently mixed, methanol was removed and then heat treatment was performed in an inert gas atmosphere. In this case, the heat treatment might be performed at 230° C. to 320° C. for 10 minutes to 4 hours (nanoparticle formation step). After the heat treatment was finished and a cooling process was performed to a room temperature, a colloidal nanophosphor having a diameter of 2 nm to 60 nm was obtained. The nanophosphor obtained as described above was washed with acetone or ethanol and then was dispersed and stored in a non-polar solvent such as hexane, cyclohexane, or chloroform.

FIG. 20 illustrates a TEM image of the nanophosphor according to Embodiment 11 of the present invention, and shows that the diameter of the nanophosphor is increased due to formation of the first shells.

Figure 21:
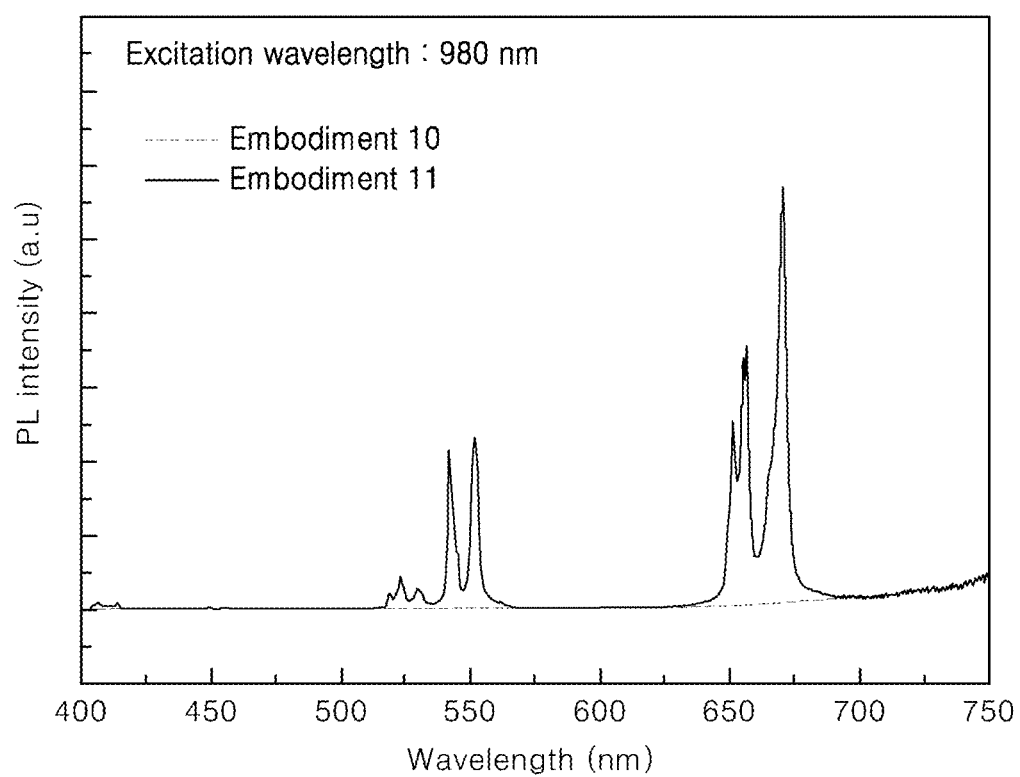
FIG. 21 illustrates PL spectra of the core and core/first shell upconversion nanophosphors according to other embodiments of the present invention under 980-nm infrared excitation.

FIG. 21 illustrates PL spectra of the nanophosphors according to Embodiments 10 and 11 of the present invention. It is shown that the PL intensity is greatly increased due to formation of the first shells around the cores.

As described above, according to an embodiment of the present invention, an upconversion nanophosphor capable of emitting high-purity red light under 980-nm, 800-nm, and 1532-nm near infrared excitation may be obtained, and photoblinking may be prevented and a high photostability may be achieved because emission of light due to electronic transition of a lanthanide element is used. Furthermore, because a biohazard risk is low, infrared light of a wavelength band of which absorption by cells is low is used as an excitation source, a diameter is equal to or less than 20 nm, and red light having a high bio-transmittance is emitted, the upconversion nanophosphor of the present invention may be appropriately used for bioimaging compared to existing upconversion nanophosphors, and may be used as an magnetic resonance imaging (MRI) contrast agent. In addition, because red light may be emitted simultaneously by light of various wavelengths, the upconversion nanophosphor of the present invention may be applied to the security field. Because most existing upconversion nanophosphors emit green or blue light by absorbing 980-nm infrared light, when the upconversion nanophosphor of the present invention is applied to the security field, a great improvement in security may be expected. Besides, because infrared light of different wavelengths may be converted into visible light recognizable with the naked eyes, the upconversion nanophosphor of the present invention may be used for a sensor for detecting infrared light. However, the scope of the present invention is not limited to the above-described effects.

While the present invention has been particularly shown and described with reference to embodiments thereof, it will be understood by one of ordinary skill in the art that various changes in form and details may be made therein without departing from the scope of the invention as defined by the following claims. The embodiments should be considered in a descriptive sense only and not for purposes of limitation. Therefore, the scope of the invention is defined not by the detailed description of the invention but by the following claims, and all differences within the scope will be construed as being included in the present invention.

What is claimed is:

1. A fluoride nanophosphor comprising a luminescent nanoparticle core represented by Chemical Formula 1

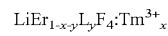

$$\text{LiEr}_{1-x-y}\text{L}_y\text{F}_4:\text{Tm}^{3+}_x \qquad \text{Chemical Formula 1}$$

wherein in Chemical Formula 1,
x is a real number satisfying 0.003≤x≤0.3, y is a real number satisfying 0≤y≤0.8, and 0.003≤x+y≤0.9, and
L, if present, is yttrium, lanthanum, cerium, praseodymium, neodymium, promethium, samarium, europium, gadolinium, terbium, dysprosium, holmium, ytterbium, lutetium, or a combination thereof.

2. The fluoride nanophosphor of claim 1, further comprising a first shell surrounding at least a portion of the core,
wherein the first shell is represented by Chemical Formula 2

$$\text{LiGd}_{1-p-q}\text{M}_q\text{F}_4:\text{Yb}^{3+}_p \qquad \text{Chemical Formula 2}$$

wherein in Chemical Formula 2,
p is a real number satisfying 0≤p≤1, q is a real number satisfying 0≤q≤1, and 0≤p+q≤1, and
M, if present, is Y, La, Ce, Pr, Nd, Pm, Sm, Eu, Tb, Dy, Ho, erbium, thulium, Lu, or a combination thereof.

3. The fluoride nanophosphor of claim 2, wherein the core and the first shell combined has a diameter of 2 nanometers to 60 nanometers.

4. The fluoride nanophosphor of claim 2, further comprising a second shell surrounding at least a portion of the first shell,
wherein the second shell is represented by Chemical Formula 3

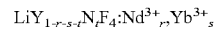

$$\text{LiY}_{1-r-s-t}\text{N}_t\text{F}_4:\text{Nd}^{3+}_r,\text{Yb}^{3+}_s \qquad \text{Chemical Formula 3}$$

wherein in Chemical Formula 3,
r is a real number satisfying 0<r≤1, s is a real number satisfying 0≤s≤0.5, t is a real number satisfying 0≤t≤1, and 0<r+s+t≤1, and
N, if present, is La, Ce, Pr, Pm, Sm, Eu, Gd, Tb, Dy, Ho, Tm, Lu, or a combination thereof.

5. The fluoride nanophosphor of claim 4, wherein the core, the first shell, and the second shell has combined a diameter of 3 nanometers to 80 nanometers.

6. The fluoride nanophosphor of claim 4, further comprising a third shell surrounding at least a portion of the second shell,
wherein the third shell is represented by Chemical Formula 4

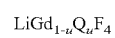

$$\text{LiGd}_{1-u}\text{Q}_u\text{F}_4 \qquad \text{Chemical Formula 4}$$

wherein in Chemical Formula 4,
u is a real number satisfying 0≤u≤1, and
Q, if present, is Y, La, Ce, Pr, Sm, Eu, Tb, Dy, Ho, Yb, Er, Lu, or a combination thereof.

7. The fluoride nanophosphor of claim 6, wherein the core, the first shell, the second shell, and the third shell combined has a diameter of 4 nanometers to 100 nanometers.

8. The fluoride nanophosphor of claim 1, wherein the core has a diameter of 1 nanometer to 40 nanometer.

9. The fluoride nanophosphor of claim 1, wherein the fluoride nanophosphor emits red light following excitation with light source having a wavelength other than 980 nanometers.

10. A method of preparing a fluoride nanophosphor, the method comprising:
forming a complex mixture of an erbium precursor, a thulium precursor, and optionally, a first precursor;
adding oleic acid and 1-octadecene to the complex mixture to provide a first mixture solution, and heating the first mixture solution;
adding a second mixture solution comprising a lithium precursor, a fluorine precursor, and an alcohol to the previously heated first mixture solution;
removing the alcohol from the reaction solution to form a complex residue; and
conducting a heat treatment of the complex residue,
wherein the nanoparticles comprise fluoride nanoparticles doped with $Er^{3+}$ and represented by Chemical Formula 1, and
wherein the first precursor comprises a yttrium precursor, a lanthanum precursor, a cerium precursor, a praseodymium precursor, a neodymium precursor, a promethium precursor, a samarium precursor, an europium precursor, a gadolinium precursor, a terbium precursor, a dysprosium precursor, a holmium precursor, a ytterbium precursor, a lutetium precursor, or a combination thereof $$LiEr_{1-x-y}L_yF_4:Tm^{3+}_x \qquad \text{Chemical Formula 1}$$

wherein in Chemical Formula 1, x is a real number satisfying 0.003≤x≤0.3, y is a real number satisfying 0≤y≤0.8, and 0.003≤x+y≤0.9, and
L, if present, is derived from the first precursor.

11. The method of claim 10, wherein the heat treatment of the complex residue is conducted at a temperature range of 230° C. to 320° C.

12. A polymer composite comprising the fluoride nanophosphor of claim 1.

13. A display device comprising the fluoride nanophosphor of claim 1.

14. A fluorescent contrast agent comprising the fluoride nanophosphor of claim 1.

15. An anti-counterfeiting film comprising the fluoride nanophosphor of claim 1.

16. A magnetic resonance imaging (MRI) contrast agent comprising the fluoride nanophosphor of claim 1.

17. A fluoride nanophosphor comprising a luminescent nanoparticle core represented by Chemical Formula 1

$$LiEr_{1-x-y}L_yF_4:Tm^{3+}_x \qquad \text{Chemical Formula 1}$$

wherein in Chemical Formula 1,
x is a real number satisfying 0≤x≤0.3, y is a real number satisfying 0≤y≤0.8, and 0≤x+y≤0.9, and
L, if present, is yttrium, lanthanum, cerium, praseodymium, neodymium, promethium, samarium, europium, gadolinium, terbium, dysprosium, holmium, ytterbium, lutetium, or a combination thereof; and
a first shell surrounding at least a portion of the core,
wherein the first shell is represented by Chemical Formula 2

$$LiGd_{1-p-q}M_qF_4:Yb^{3+}_p \qquad \text{Chemical Formula 2}$$

wherein in Chemical Formula 2,
p is a real number satisfying 0≤p≤1, q is a real number satisfying 0≤q≤1, p and q satisfies 0≤p+q≤1, and
M, if present, is Y, La, Ce, Pr, Nd, Pm, Sm, Eu, Tb, Dy, Ho, erbium, thulium, Lu, or a combination thereof.

18. The fluoride nanophosphor of claim 17, further comprising a second shell surrounding at least a portion of the first shell,
wherein the second shell is represented by Chemical Formula 3

$$LiY_{1-r-s-t}N_tF_4:Nd^{3+}_r,Yb^{3+}_s \qquad \text{Chemical Formula 3}$$

wherein in Chemical Formula 3,
r is a real number satisfying 0≤r≤1, s is a real number satisfying 0≤s≤0.5, t is a real number satisfying 0≤t≤1, and r+s+t satisfies 0≤r+s+t≤1, and
N is La, Ce, Pr, Pm, Sm, Eu, Gd, Tb, Dy, Ho, Tm, Lu, or a combination thereof.

19. The fluoride nanophosphor of claim 18, further comprising a third shell surrounding at least a portion of the second shell,
wherein the third shell is represented by Chemical Formula 4

$$LiGd_{1-u}Q_uF_4 \qquad \text{Chemical Formula 4}$$

wherein in Chemical Formula 4,
u is a real number satisfying 0≤u≤1, and
Q, if present, is Y, La, Ce, Pr, Sm, Eu, Tb, Dy, Ho, Yb, Er, Lu, or a combination thereof.

20. An article comprising the fluoride nanophosphor of claim 17, wherein the article is a display device, a fluorescent contrast agent, an anti-counterfeiting film, or a magnetic resonance imaging contrast agent.

* * * * *